United States Patent [19]

King

[11] 4,100,916
[45] Jul. 18, 1978

[54] THREE-DIMENSIONAL ULTRASONIC IMAGING OF ANIMAL SOFT TISSUE

[76] Inventor: Donald L. King, 19 Searles Rd., Darien, Conn. 06820

[21] Appl. No.: 680,885

[22] Filed: Apr. 27, 1976

[51] Int. Cl.² ............................................. A61B 10/00
[52] U.S. Cl. .................................................. 128/2 V
[58] Field of Search .................. 128/2 V, 2 S, 205 Z, 128/24 A; 73/67.8 S

[56] References Cited

U.S. PATENT DOCUMENTS

| | | | |
|---|---|---|---|
| 2,559,227 | 7/1951 | Rieber | 128/24 A |
| 3,555,888 | 1/1971 | Brown | 93/67.8 |
| 3,688,564 | 9/1972 | McDicken | 73/67.8 S |
| 3,744,479 | 7/1973 | Owens et al. | 128/2 S |
| 3,777,740 | 12/1973 | Hokanson | 128/2 V |
| 3,789,833 | 2/1974 | Bom | 128/2 V |
| 3,822,694 | 7/1974 | Mills et al. | 128/2 S |
| 3,881,466 | 5/1975 | Wilcox | 128/2 V |
| 3,909,771 | 9/1975 | Pickering et al. | 73/67.8 S X |

OTHER PUBLICATIONS

Brown, "Ultrasonics", vol. 5, Apr. 1967, pp. 118–124.
Dekker et al., "Computers & Biomedical Research", vol. 7, 1974, pp. 544–553.
Kossoff, "Jorunal of Clinical Ultrasound", vol. 2, No. 1, 1974, pp. 61–72.
Robinson, "The Journal of the Acoustical Society of America", vol. 52, 1971, pp. 673–687.
Wells, "Physical Principles of Ultrasonic Diagnosis", Academic Press, London–New York, 1969, pp. 186–188 & 246.
Fry et al., "Journal of the Acoustical Society of America", vol. 44, No. 5, 1968, pp. 1324–1338.
Baum et al., New York State Journal of Medicine", vol. 61, No. 24, Dec. 15, 1961, pp. 4149–4157.
Howry et al., "Journal of Applied Physiology", vol. 9, No. 2, Sep. 1956, pp. 304–306.
"Sonix", vol. 1, Nos. 4 & 5, Jul.–Aug. 1975, p. 16.
King, "Journal of Clinical Ultrasound", vol. 1, No. 3, Sep. 1, 1973, pp. 196–201.
Science Accessories Corp., Publication No. S GP-2-3-0-23 (2 pages) on "Graf/pen" Sonic Digitizer.
Chow et al., "IBM Technical Disclosure Bulletin", vol. 17, No. 10, pp. 3154–3158, Mar. 1975.

*Primary Examiner*—William E. Kamm
*Attorney, Agent, or Firm*—Buell, Blenko & Ziesenheim

[57] ABSTRACT

An apparatus for collecting three-dimensional data on the size, shape, location and nature of animal soft tissue organ structures within the animal and reconstructing the data outside the animal. The apparatus provides a representation of the size, shape, location and nature of the structure in three dimensions.

16 Claims, 8 Drawing Figures

Scheduler/Controller Block Diagram (10)

Fig. 4A. Scheduler/Controller

Fig. 4B.

Fig. 5A. Analog To Digital Converter

THREE-DIMENSIONAL ULTRASONIC IMAGING OF ANIMAL SOFT TISSUE

This invention relates to three-dimensional ultrasonic imaging of animal soft tissue. More particularly, it relates to an apparatus for collecting three-dimensional data on the size, shape, location and nature of animal soft tissue organ structures within the animal and reconstructing the data outside the animal to provide a representation of the size, shape, location and nature of the structure in three dimensions.

THE PROBLEM PRESENTED TO THE INVENTOR

The problem presented to the inventor, Donald L. King, M.D., was to conceive and develop an apparatus capable of collecting three-dimensional data on the size, shape, location and nature of animal soft tissue organ structures within the animal and reconstructing the data outside of the animal to provide a representation of the size, shape, location and nature of the structure in three dimensions.

This apparatus is useful in medical diagnosis. For example, it provides a safe, reliable and effective, non-invasive means for diagnosis of the heart. The apparatus uses inter alia ultrasonic imaging techniques.

Diagnostic ultrasonic instruments employing the pulse/echo-ranging principle have evolved from comparatively simple to complex devices. This evolution has improved their usefulness by a quantitative and qualitative increase in the data that they acquire, process and display. The data input for these systems consists of the echo range and amplitude pulse spatial coordinates and time.

A general problem faced by medical ultrasonic instruments of the type described is the specular nature of ultrasound reflections from tissue structures. Larger surfaces and structures in the body, such as the heart valves and walls, tend to act as mirror-like reflectors in which the angle of reflection equals the angle of incidence. For echo-ranging instruments in which the reflected sound wave must return to a transmitting transducer the angle of incidence must be nearly perpendicular to the reflecting structure. In the body, the geometry and orientation of reflecting surfaces is highly variable and complex. Therefore, to optimize the echo return from any given point on a reflecting surface of unknown orientation the point on the surface should be scanned by the ultrasound beam from every possible direction. To realize this ideal an ultrasound scanner should therefore be capable of scanning freely in three dimensions.

A specific problem encountered when imaging the heart with ultrasonic techniques is the relatively small aperture or window through which the ultrasound beam may be passed from the anterior chest. Only a small surface of the anterior heart is directly opposed to the chest wall without intervening lung or bone blocking the passage of the ultrasonic waves. Through this small window (aperture) the sound beam may be angled in a great variety of directions to collect echo data. By use of an instrument capable of randomly scanning in any direction more echoes may be collected than by means of an instrument constrained in its scanning to a fixed pattern such as serial parallel planes.

The simplest medical ultrasonic instruments record and display only echo amplitude and the range of an echo source from the ultrasound transducer-one spatial dimension. This has been improved for evaluation of the moving heart by creation of a time-motion display in which echo range is presented as a function of time. For pictorial evaluation of an anatomic structure ultrasound scanners have been constructed. A scanner is a device for registering the spatial orientation of the ultrasound transducer, and hence for producing the spatial coordinates of each echo source. Conventional ultrasonic scanners confine the movement of the transducer and the sound beam to a plane. As a consequence they generate only two spatial coordinates, X and Y, for each echo source. Movement of the transducer in a plane may consist of simple linear, arc or sector scans, or various combinations of these, that is, compound scanning. Compound scanning increases the number of specular echoes that may be collected. Nevertheless echoes collected by compound scanning in a plane represent only a portion of those potentially available from within the plane. A tissue structure or surface oblique to the scanning plane will reflect the ultrasound waves out of the scanning plane. Incorporation of such an obliquely reflected echo into the planar image would require a three-dimensional scanning system that registers X, Y and Z coordinates for each echo source. In addition it would require a three-dimensional image memory and integration device.

Conventional scanners developed as two-dimensional systems because image integration and image display were combined into a single device such as an oscilloscope/film combination which was a two-dimensional system and capable of integrating only two-dimensional data. The registration of transducer movement was limited to two dimensions by the image-memory format. The plane of the oscilloscope screen (the image plane) had to have a direct correspondence to the tissue plane under examination. Therefore, scanners were built as two-dimensional scanners. Echoes could only be collected from within the tissue plane being scanned. Such an analog system had no capability for storing and/or integrating into a planar image echoes recorded outside the tissue plane giving rise to the echoes and corresponding to the image plane. There was no memory means for dissociating the direct correspondence of the scanning plane and the image integration and display plane. Three-dimensional scanning, to be successful, would require separation of these two functions, namely, image integration and image display. The former would have to be performed by a device such as a computer capable of three-dimensional memory. A three-dimensional scanning and a three-dimensional memory system would not only solve the problem of specular echo reflection and separate image integration and display functions but would also create an image volume of a tissue volume. This system would register the relationship to one another of sequentially obtained echo data whether acquired by parallel or non-parallel planar scans or by other scanning formats such as spiral scanning. From the three-dimensional computer memory, suitably processed images in any two-dimensional cross-sectional plane could be retrieved. Also, computer graphic techniques such as perspective, rotation and shading could be used to simulate three-dimensional images.

A practical problem in three-dimensional scanning is the time required for its completion. Conventional two-dimensional scanners take several seconds to complete an image of the body, a slow rate of image formation compared to body organ movement caused by cardiac pulsation or respiration. Use of sequential planar scans of this type in three dimensions would be too time consuming to be practical. However, a sub-group of two-dimensional scanners, known as real-time scanners, has a high rate of image formation and regeneration relative to structure motion (greater than 15 per second). This feature incorporates the dimension of time into the pictorial display and produces a dynamic image. Real-time scanners do simple scans and alone cannot perform three-dimensional compound scanning. For purposes of three-dimensional scanning the real-time scanner greatly augments the rate of data acquisition that is spatially oriented by distinct coordinates. Integration of the real-time scanner into a three-dimensional scanning apparatus permits rapid data acquisition as well as registration of three echo source coordinates.

THE PRIOR ART

Brown, U.S. Pat. No. 3,555,888 (see also Brown TG: Visualization of Soft Tissues in Two and Three Dimensions — Limitations and Development. Ultrasonics 5:118, 1967) has been proposed for three-dimensional ultrasonic scanning. This apparatus utilizes a mechanical linkage with five potentiometers to register the position of the ultrasound transducer in three dimensions during a scan. It utilizes an oscilloscope (cathode ray tube) for display and a control means by which echoes are selected for display from a particular plane section of the body. It does not utilize a three-dimensional memory, either digital computer or otherwise, to retain three-dimensional echo data information. It integrates and displays data arising only from a two-dimensional internal body plane on a two-dimensional oscilloscope.

A similar apparatus utilizing a digital computer for three-dimensional memory and image integration has recently been reported (Dekker DL, et al: A System for Ultrasonically Imaging the Human Heart in Three Dimensions. Computers and Biomedical Research 7:544–553, 1974). This apparatus utilizes a five degree of freedom mechanical arm with one potentiometer for each axis of rotation. A single conventional transducer rather than a real-time scanner is used in the system for data acquisition. As a consequence the time required to form a complete three-dimensional image of a time varying structure such as the heart is impractically long.

Three-dimensional scanners with mechanical linkages have the disadvantage of inflexibility due to inertia and friction. The mechanical linkage can be cumbersome and in the way of the operator. Registration accuracies achievable with mechanical systems may be less than desired and deteriorate with usage.

Other art prepared in this area include:

(a) Kossoff G: Display Techniques in Ultrasound Pulse Echo Investigation: A Review. J. Clin Ultrasound 2:61, 1974. This article reviews the techniques for three-dimensional displays of combinations of two-dimensional echograms and points out their limitations.

(b) Rasmussen SN, Nielsen SS, Bartrum RJ, et al: Three-dimensional Imaging of Abdominal Organs with Ultrasound. Am. J. Roentgen. 121:883, 1974. This article describes the computer reconstruction of three-dimensional images from a series of two-dimensional B-scans digitized by means of a pencil follower.

(c) Robinson DE: Display of Three-dimensional Ultrasonic Data for Medical Diagnosis. J. Acoust. Soc. Amer: 52:673, 1971. This article also concerns a similar process of three-dimensional image reconstruction from a series of parallel two-dimensional images and the formation of new two-dimensional images through the three-dimensional information.

The techniques described in the preceding three articles utilize echo data collected in a two-dimensional scanning system. The addition of the third assumed coordinate to the data base is carried out by the operator when entering the data into the computer.

(d) Physical Principles of Ultrasonic Diagnosis. Wells, PNT. Academic Press, London, 1969. This text discusses the problem of specular reflection and various three-dimensional display techniques.

(e) Fry WJ, Leichner GH, Okuyama D, et al: Ultrasonic Visualization System Employing New Scanning and Presentation Methods. J. Acous. Soc. Amer. 44:1324, 1968. This article describes a computer-based system for omni-directional scanning. The scanning system is a mechanical apparatus utilizing three translational and two rotational degrees of freedom. A single planar image is formed by scanning within the tissue plane corresponding to the image plane and by scanning at angular orientations to the plane of section. Time gating is used to present only appropriate echoes when scanning at an angle to the tissue plane section. Scanning at an angular orientation is achieved by rotating the object being scanned.

(f) Baum G, Greenwood I: Orbital Lesion Localization by Three-dimensional Ultrasonography. N.Y. State J. Med. 61:4149, 1961. This article describes construction of a three-dimensional model by arranging a series of two-dimensional ultrasonogram tansparencies in a series of transparent (glass) blank spacers.

(g) Howry, DH, Posakony G, Cushman CR, et al: Three-dimensional and Stereoscopic Observation of Body Structures by Ultrasound. J. Applied Physiol. 9:304, 1956. This article describes a mechanical apparatus for scanning a limited volume in three dimensions. A two-dimensional variable perspective projection of the volume is displayed on an oscilloscope.

DEFINITION OF TERMS

SOFT TISSUE ORGAN STRUCTURES — non-skeletal, non-osseous components of the body such as the heart, kidneys, blood and blood vessels, liver, and the like.

ULTRASONIC REAL-TIME SCANNER (FIRST MEANS) — a medical diagnostic instrument producing instantaneous and continuous images of soft tissues that depict movement as it occurs by means of acoustical waves in the frequency range of 1–20 mHz, such as a device known as "Multiple Crystal Cardiac Scanner" manufactured by Hoffrel Instruments, Inc., Moody's Lane, Norwalk, Conn.

A similar device is manufactured by Organon Teknika B.V. Industrielaan 84, OSS, Holland and is referred to as the "ECHOCARDIOVISOR System". These two devices have been advertised in a publication "Sonix" July–August 1975 Vol. 1, No. 4-5 at page 16.

This type of device is also shown in U.S. Pat. Nos. 3,881,466 and 3,789,833. It is also referred to in a published article "Real-Time Cross-sectional Ultrasonic Imaging of the Heart Using a Linear Array Multi-element Transducer," by Donald Latham King, M.D., printed in *Journal of Clinical Ultrasound*, September 1973, Vol. 1, No. 3, Pages 196–201.

SONIC LOCATOR (SECOND MEANS including: transmitter means; and sensor means) — a device for sensing the location of a point of points in space using hypersonic waves orginating at the point or points generated by means of spark gaps and traveling through air to acoustical wave sensors. The sensors detect the arrival of the waves and the device converts the transit time of the waves to electronic signals representing the spatial coordinates of the point or points.

Such a device is commercially manufactured and available from Science Accessories Corporation of Southport, Conn., and is termed a Three-dimensional Graf/Pen Sonic Digitizer, GP-3 3-D type SGM 1.

COMPUTER — a digital computer for processing, storing and displaying numeric data consisting of a central processor, core memory, magnetic tape and disk storage, input/output keyboard and typewriter and video display terminal. Such a computer is available from the Digital Equipment Corporation, Maynard, Massachusetts, known as the PDP 11/45, including appropriate peripheral devices.

Electrocardiograph — an instrument which detects the voltage produced by the heart. The particular device used in this specification is manufactured by Hoffrel Instruments, Inc., is sold as part of their real-time scanner and designated "model 704 EKG Slow Sweep Module".

MEASURABLE PHYSICAL CHARACTERISTICS OF ACOUSTICAL WAVES — properties of acoustical waves or of pulses of acoustical waves such as:

(a) velocity;
(b) transit time;
(c) frequency;
(d) wave length;
(e) phase;
(f) amplitude or intensity;
(g) pulse duration; and
(h) direction of propagation.

DESCRIPTION OF PREFERRED EMBODIMENT

This invention utilizes a non-mechanical, non-contacting position sensing apparatus for three-dimensional scanning. This apparatus is to be used in combination with a type of ultrasound scanner known as a real-time scanner and also in combination with a digital computer and its associated interfaces and peripheral devices. This combination improves three-dimensional scanning in conjunction with three-dimensional computer memory, processing and graphic display techniques to provide ultrasonic diagnostic images of qualitatively and quantitatively increased information content and therefore increased diagnostic usefulness.

It must be understood that the three-dimensional representation of the soft tissue is data in the computer. The readout of data from the computer may be in two dimensions (eg. print-out sheets) which can then be read or interpreted in three dimensions.

The position-sensing apparatus for three-dimensional scanning is a sonic locater (sonic digitizer). Its purpose is to track the location in space of the ultrasonic probe of the real-time scanner. It measures the transit time of a hypersonic wave front from a point source such as a spark gap, to a sensor array of three orthogonal linear microphones over the patient. A sound velocity for ambient conditions (temperature, pressure, humidity) is assumed and the distance of the source from the sensors is calculated. Output consists of digital signals representing the X, Y and Z coordinates of the point. If the direction of a line in space is to be recorded two spark gaps are utilized. In order to orient and record the position of an object in space such as an ultrasound probe three spark gaps fired in a known repeatable sequence defining a plane are required. The three spark gaps are mounted in close proximity in a triangular arrangement on a plastic board. This board is mechanically attached in a fixed, rigid manner to the ultrasound transducer probe.

As the probe moves the three spark gaps are fired in a continuous sequence and the sonic locater constantly tracks their position and orientation in space. The probe may be moved freely and randomly anywhere within the volume defined by the microphones while maintaining a direct line of sight from each spark gap to each microphone. From the position coordinates of the spark gaps and from the echo range and sequence data from the real-time scanner may be calculated the X, Y and Z position coordinates of the ultrasound probe and subsequently those of each echo source. The position coordinates of the spark gaps, the ultrasound data, timing or synchronizing signals from the real-time scanner and the patient's electrocardiogram are digitized and stored in computer memory. From this data base by a suitable coordinate transformation the ultrasound data is assembled into a single three-dimensional body image matrix. The three-dimensional matrix then can be displayed in two-dimensional cross-sectional form or as simulated three-dimensional images using perspective, shading, rotation, animation and so forth. Mathematical determination of heart volume and wall motion velocity can also be carried out.

In comparison to conventional two-dimensional ultrasonic scanners the probe of this apparatus scans over the body surface randomly and freely in three dimensions. As a consequence it solves the general problem of specular echo reflections by permitting the transducer probe to be positioned optimally for collection of any given echo and it permits data collection for a maximum number of directions via the small access window to the heart in the anterior chest wall. In comparison to two-dimensional systems it integrates the ultrasonic image in three dimensions in computer memory permitting subsequent display in the cross-section or projection most satisfactory for diagnosis rather than for data collection. In comparison to the prior art the non-contacting sonic locator is more flexible, less cumbersome and of equal or greater accuracy than mechanical linkages for three-dimensional position sensing. Further, the present apparatus resolves the problem of slow data acquisition inherent in the prior art by use of a real-time scanner.

I provide an apparatus for collecting three-dimensional data on the size, shape, location and nature of animal soft tissue organ structures within the animal and reconstructing the data outside the animal to provide a representation of the size, shape, location and nature of the structure in three dimensions which comprises a first means for generating a plurality of acoustical waves from a source, the waves are transmitted into the tissue and are then returned to a receiver, the means detects measurable physical characteristics of the returned wave, the means then produces electronic signals corresponding to the characteristics of the wave; a second means having a transmitter means which remains in a known spatial relationship with respect to the first means, the transmitter means emits a plurality of energy waves from a plurality of discrete points, the second means having a sensing means which is spaced from the transmitter means of the second means, the sensing means senses each energy wave from each discrete point of the transmitter means in three dimensions known as X, Y and Z, the second means produces electronic output signals corresponding to each wave from the plurality of discrete points; and a computer means electrically coupled to the first and second means which receives the output signals from the first and second means and by computer processing, the data transmitted by the signals is assembled and displayed in a form useful for determining the size, shape, location and nature of the tissue in three dimensions.

Other details, objects and advantages of this invention will become apparent as the following description of the present preferred embodiment proceeds.

In the accompanying drawings, I have shown a present preferred embodiment of the invention in which:

FIG. 4C is a detailed schematic diagram of a locater control circuit which forms a part of the scheduler/controller circuit shown in FIGS. 4A and 4B;

FIG. 4D is a detailed schematic of a digitizing circuit which is part of the scheduler/controller shown in FIGS. 4A and 4B;

FIG. 5A and FIG. 5B are combined FIG. 5A appears on the left and FIG. 5B appears on the right.

DETAILED DESCRIPTION OF THE PREFERRED EMBODIMENT

A. First Means 2

Figure 1:
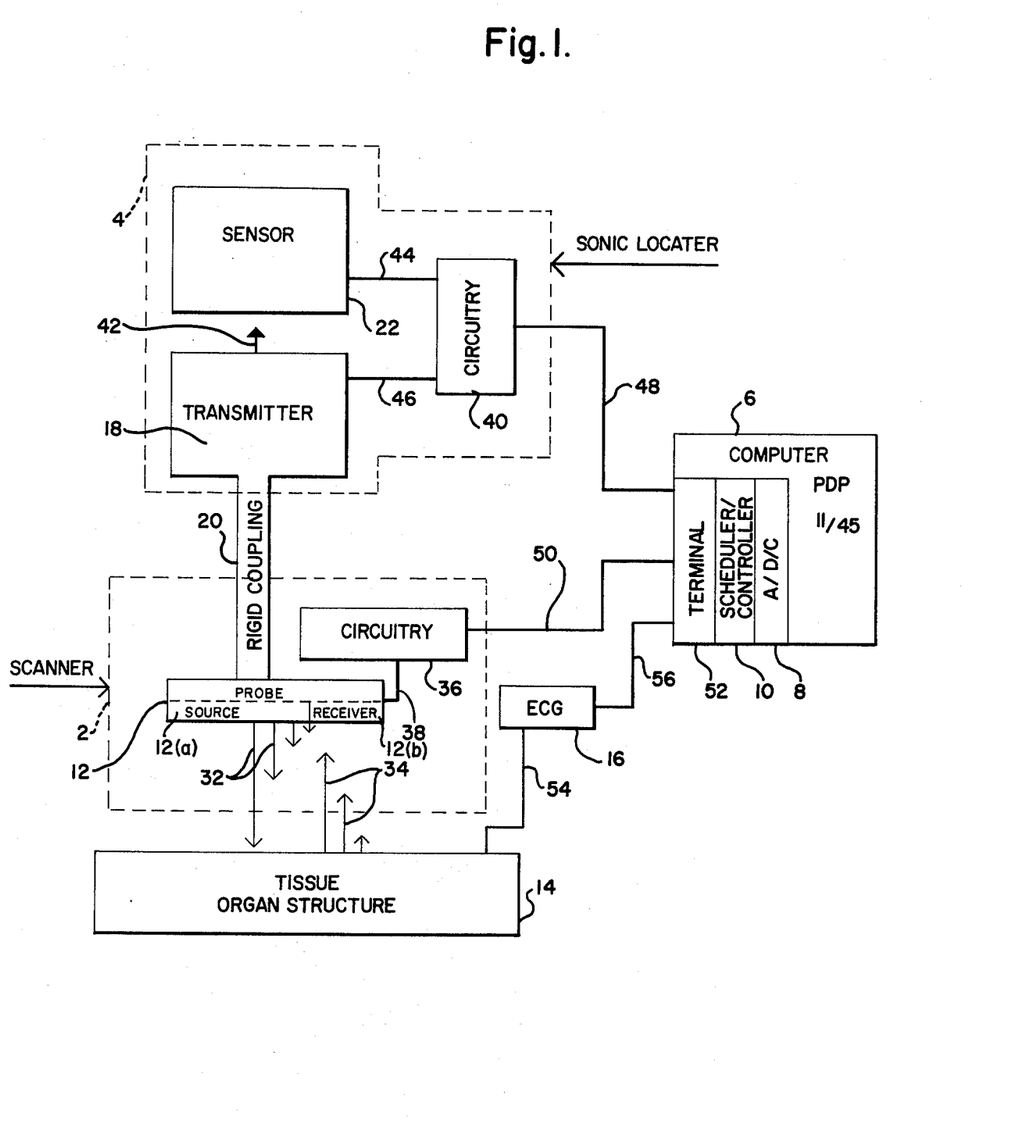
FIG. 1 is a schematic block diagram showing the system.

Referring to FIG. 1 the first means comprises an ultrasonic real-time scanner instrument 2 of the conventional type set forth earlier. It consists of a transducer probe 12 electrically coupled by a cable 38 to circuitry 36. The instrument 2 by means of crystals in the probe 12 transmits from a source 12(a) a plurality of acoustical signals (waves) 32 to an object such as a soft tissue organ of an animal 14. Acoustical signals 34 are returned from the tissue 14 to a receiver 12(b) in the probe 12. The instrument 2 detects measurable physical characteristics of the returned signals 34 as defined on page 11 and produces electronic signals corresponding to these physical characteristics. These signals and other clock and synchronizing signals are transmitted by cables 50 to terminal 52 of the computer means 6.

The electrocardiograph means 16 is a conventional instrument as set forth earlier which detects voltages produced by the heart. This means 16 is coupled to the surface of the animal 14 and the computer means 6 terminal 52 by cables 54 and 56 respectively.

B. The Second Means 4

Referring to FIG. 1 the second means 4 is shown as a sonic locater of the conventional type set forth on page 10. It comprises a transmitter 18 consisting of three spark gaps which emit acoustical waves 42 from the spark gaps. The waves 42 are sensed by sensor(s) 22 which are spaced from the transmitter 18. The transmitter 18 is capable of free movement with respect to the sensor(s) 22 which remain stationary. Both the sensor(s) 22 and the transmitter 18 are electrically coupled by cables 44 and 46, respectively, to circuitry 40. The sensor(s) 22 sense the arrival of each acoustical wave 42 from each of the three spark gaps in three dimensions known as X, Y and Z. The circuitry 40 then produces electronic output signals corresponding to each wave from the three discrete points. The electronic signals are transmitted by cable 48 to the computer means 6 at terminal 52. The transmitter 18 is rigidly coupled to the probe 12 by a rigid mechanical coupling 20 so that when the probe 12 moves in space the transmitter 18 moves correspondingly. The rigid coupling can be substituted by a means which measures the variable relationship between the transmitter 18 and probe 12.

It must be understood that the spark gap transmitter and sensor which produces and receives, respectively, acoustical waves can be replaced by an electromagnetic transmitter/sensor system.

C. Computer Means 6

Figure 5A:
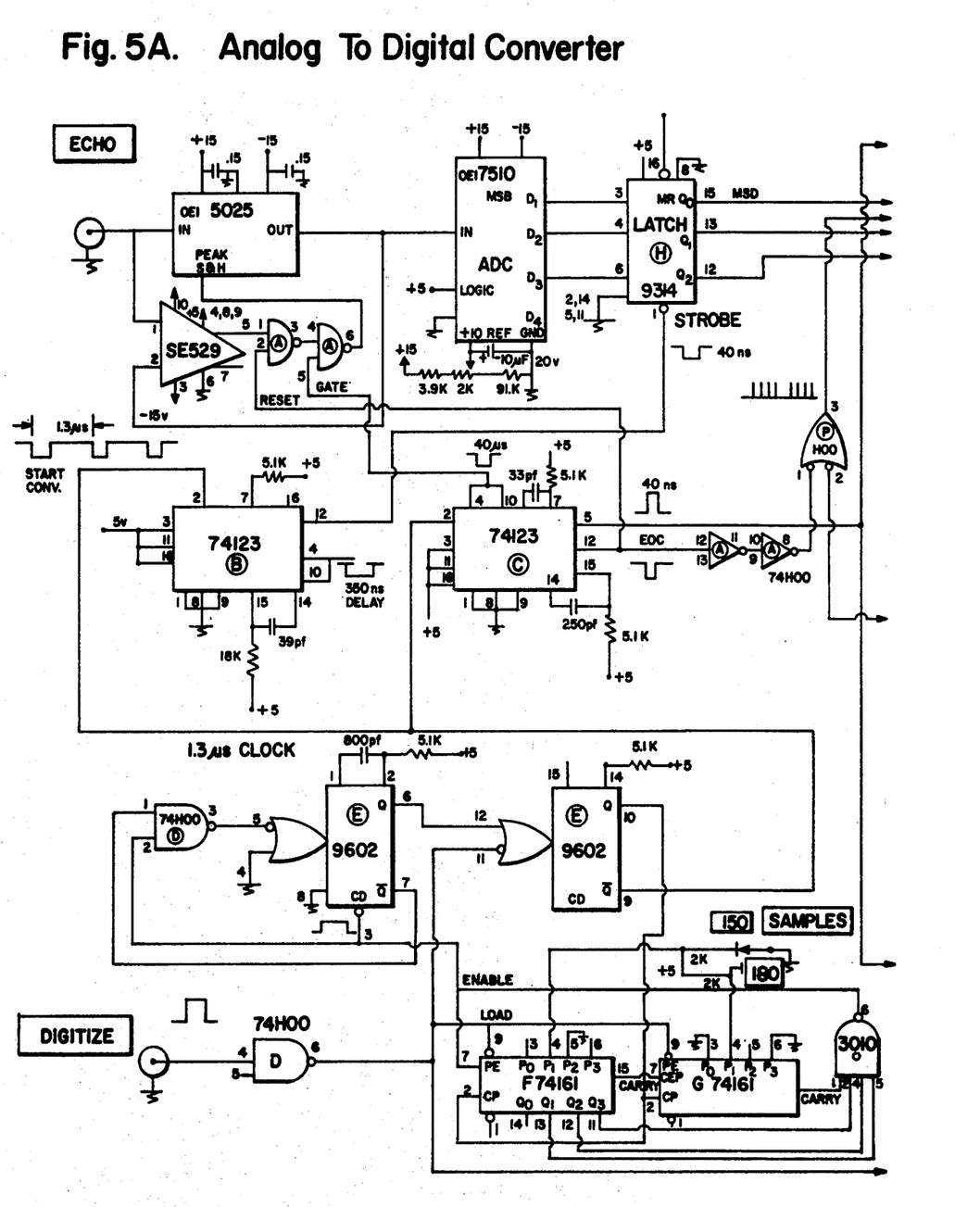
FIG. 5A is a detailed schematic diagram of the left portion of the analog-to-digital converter shown in the block diagram in FIGS. 1 and 3.
Figure 5B:
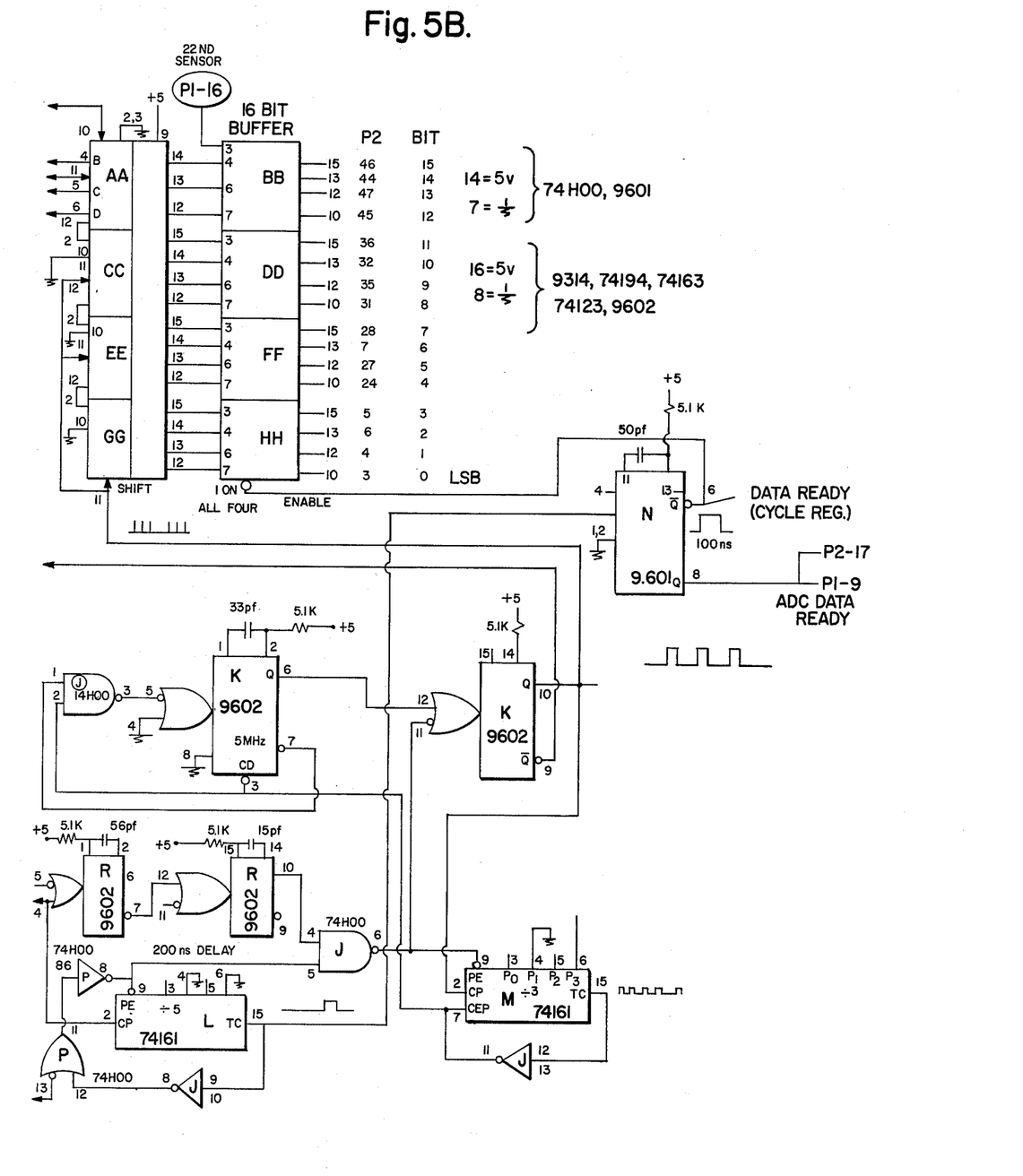
FIG. 5B is a detailed schematic diagram of the right portion of the analog-to-digital converter shown in the block diagram in FIGS. 1 and 3 and is connected to the left portion of the schematic shown in FIG. 5A. When

Referring to FIG. 1 the computer means 6 includes the conventional digital computer PDP 11/45 set forth on page 11. This computer has a terminal 52 which is electrically coupled to the sonic locater 4 (second means 4), to the ultrasonic real-time scanner 2 (first means 2) and to the electrocardiogram means 16 by cables 48, 50 and 56, respectively. The computer means 6 includes a scheduler/controller 10 which is shown in block diagram in FIG. 2 and detailed circuitry in FIG. 4A, FIG. 4B, FIG. 4C and FIG. 4D. The computer means 6 also includes an analog-to-digital converter 8 which is shown in block diagram in FIG. 3 and detailed circuitry in FIG. 5A and FIG. 5B.

Figure 2:
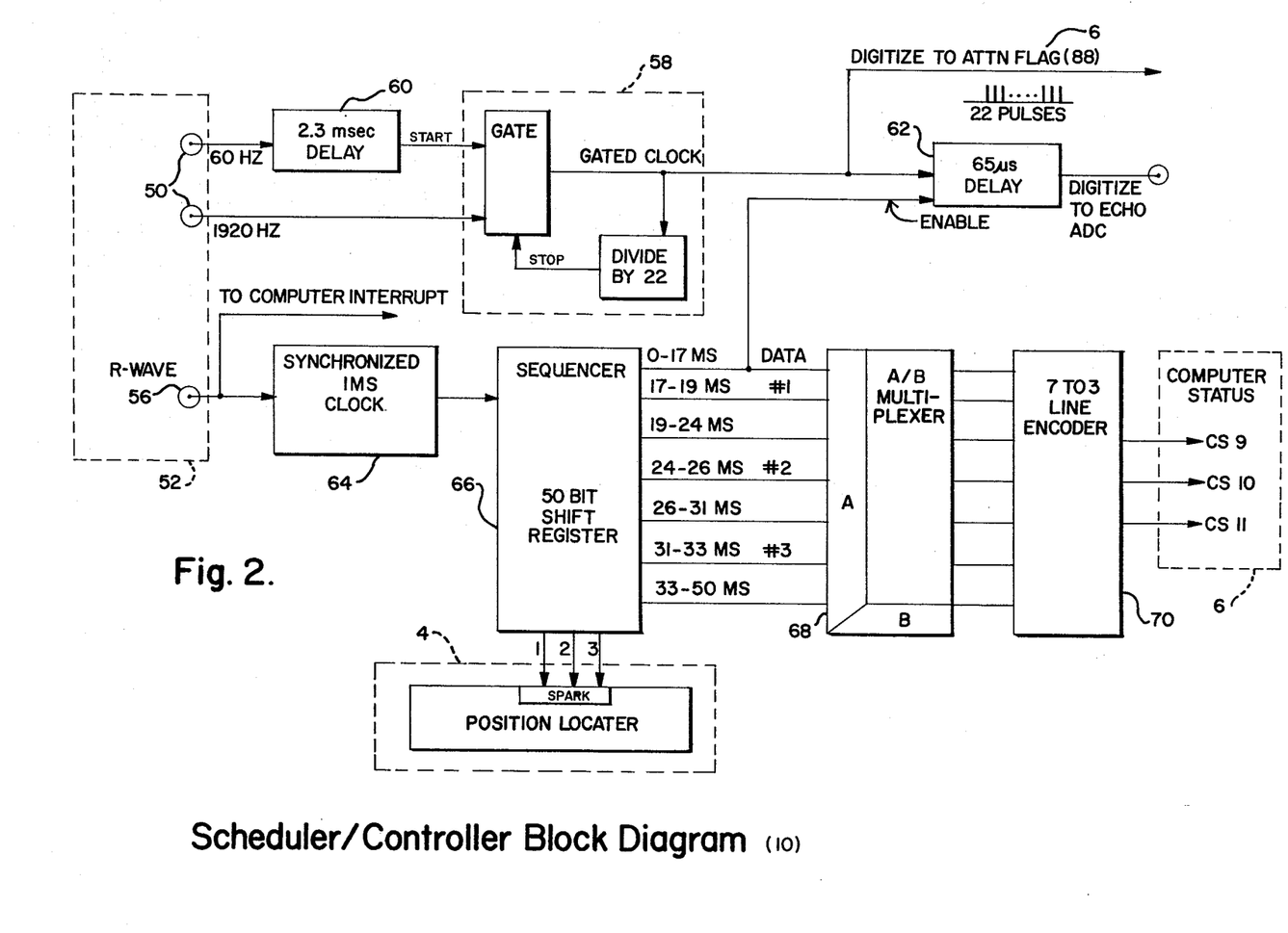
FIG. 2 is a block diagram showing the scheduler/controller system 10.

Referring to FIG. 2, the scheduler/controller consists of circuitry for controlling and sequencing digitization and acquisition of data signals from the first means 2 and second means 4 by the computer means 6. A gated clock circuit 58 receives a 60 Hertz synchronizing signal and a 1920 Hertz master clock signal. The synchronizing signal passes through a delay 60 of approximately 2.3 milliseconds and activates the gated clock circuitry passing the next twenty-two master clock pulses. These pulses set an attention flag 88 in the computer and pass to a 65 microsecond delay circuit 62. When the latter is enabled by a signal from the fifty-bit shift register the master clock pulse passes to the analog-to-digital converter 8 initiating the digitization of the data signals from the first means 2.

A signal corresponding to the R-wave of the electrocardiogram causes a computer interrupt and re-starts a 1 millisecond clock 64. Each cycle of the clock 64 sets a bit in the shift register 66. The latter defines time segments in the R—R interval. Output from the shift register controls the operational sequence of the system during each time segment. Output signals from 0-17 milliseconds enable data digitization. Signals from 17-19 milliseconds, 24—26 milliseconds and 31-33 milliseconds, respectively, activate the three individual spark gaps of the transmitter means 18 of the second means 4. Output signals also pass to a multiplexer 68 and thence to a line encoder 70 to set computer 6 status registers.

Figure 3:
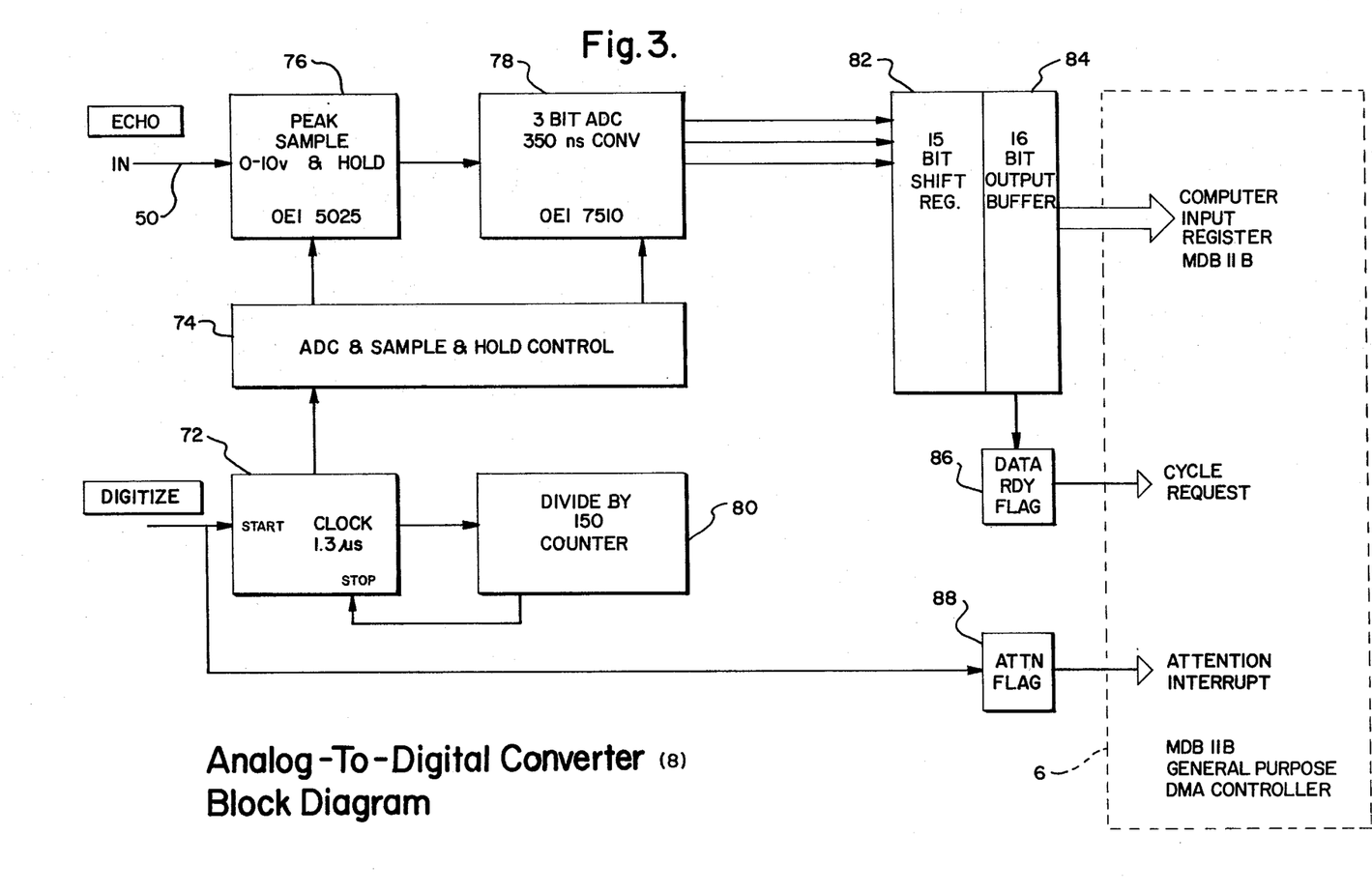
FIG. 3 is a block diagram showing the analog-to-digital converter system 8.
Figure 4A:
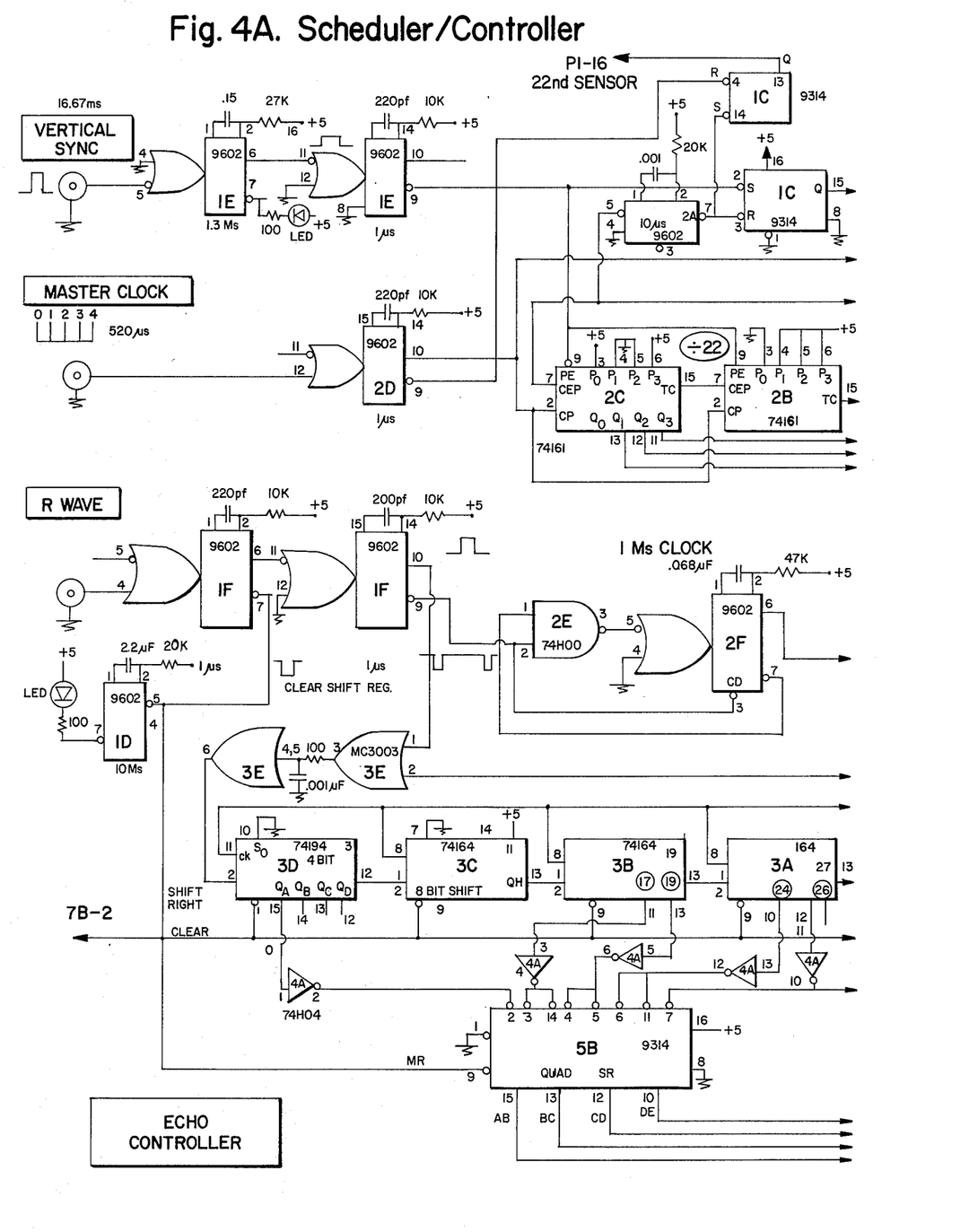
FIG. 4A is a detailed schematic diagram of the scheduler/controller shown in the block diagram in FIGS. 1 and 2. The schematic shown in this Figure is the left portion of the entire schematic for the scheduler/controller.
Figure 4B:
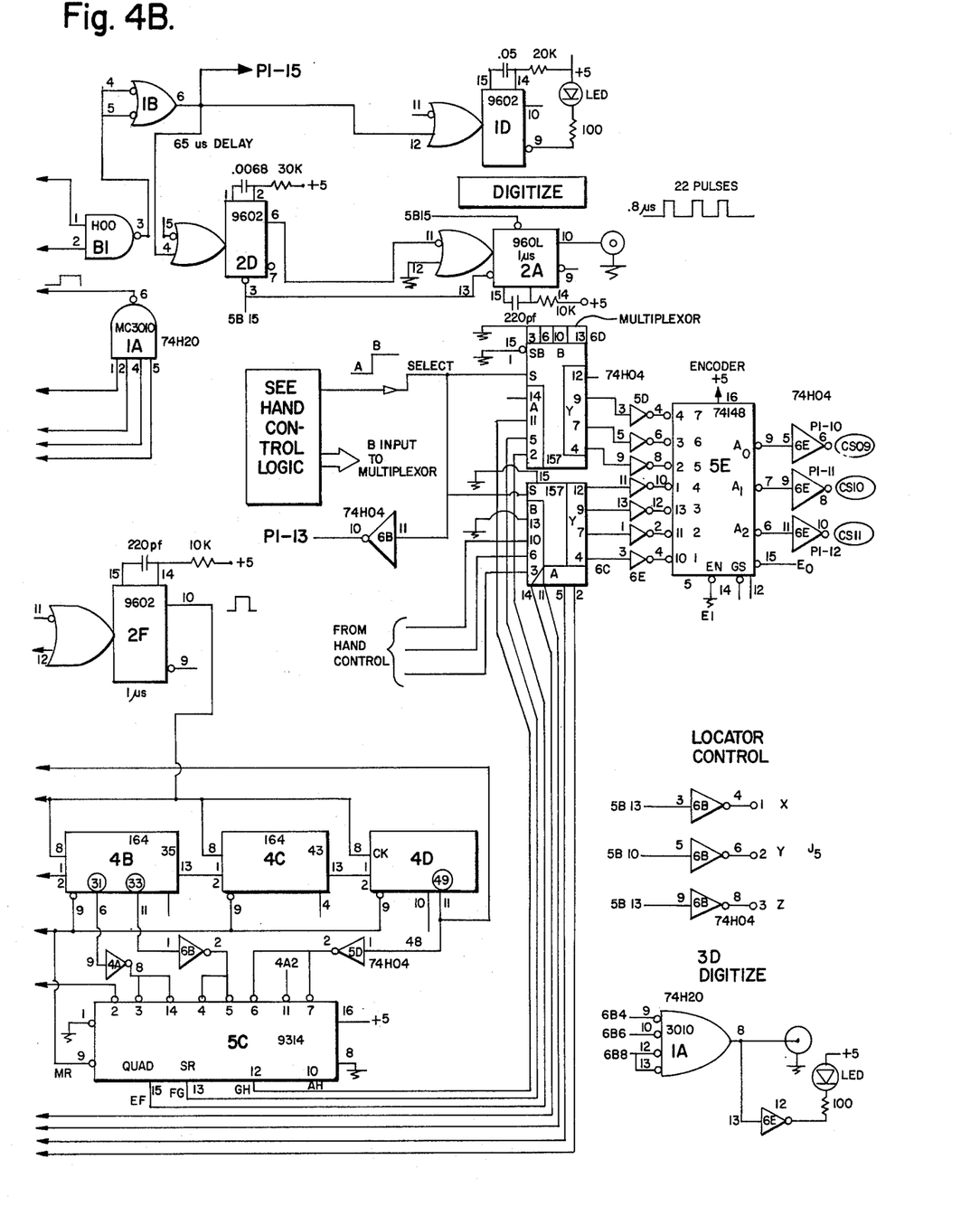
FIG. 4B is a detailed schematic diagram of the scheduler/controller shown in the block diagram in FIGS. 1 and 2 and is the right portion of the schematic which is connected to the left portion of the schematic shown in FIG. 4A.

Referring to FIG. 3, the analog-to-digital converter 8 consists of circuitry for digitizing data signals from the first means 2 in a 1.3 microsecond sample to one of eight levels for sequences of 150 samples. The digitization signal from the scheduler/controller 10 starts a 1.3 microsecond clock 72 enabling the control circuits 74 for the peak sample and hold 76 and analog-to-digital converter 78. A counter 80 terminates the sampling sequence after 150 samples until the next digitization signal. Data signals from the first means 2 arriving at the peak sample and hold 76 are repetitively sampled for each 1.3 microsecod interval and the maximum value for each interval transmitted to the analog-to-digital converter 78 where it is digited to one of eight levels using 3 bits.

The bits are set in a 15-bit shift register 82. When the shift register is filled with five samples the data is transferred to a 16-bit output buffer 84. A data ready flag 86 is set and the data subsequently transferred to the computer 6 input register.

The detail schematic diagrams of the block diagrams for the scheduler/controller system (FIG. 2) and the analog-to-digital converter system (FIG. 3) are shown in detail in FIGS. 4A-D and 5A-B, respectively. It is submitted that the schematics are detailed such that further verbal explanation of the schematics is considered unnecessary. The following is a guide to some of the components in the schematics with their respective designations and functions.

| DESIGNATION | FUNCTION | SOURCE |
|---|---|---|
| 5025 | Sample and hold | Optical Electronics, Inc. |
| 7510 | 4-bit analog-to-digital converter | Optical Electronics Inc. |
| SE529 | Comparator | Signetics |
| 9314 | Quad latch set-reset | Fairchild Semiconductor |
| 9601 | Single one-shot | Fairchild Semiconductor |
| 9602 | OR gate on input of dual one-shot | Fairchild Semiconductor |
| 74H00 | NAND Gate | Texas Instruments |
| 74123 | Dual one-shot | Texas Instruments |
| 74H04 | Hex inverter | Texas Instruments |
| 74194 | Shift register | Texas Instruments |
| 74161 | Programmable Counter | Texas Instruments |
| 74162 | Programmable Counter | Texas Instruments |
| 74164 | Shift register - 8-bit | Texas Instruments |
| 74157 | Multiplexor | Texas Instruments |
| 74148 | 7:3 Encoder | Texas Instruments |
| MC3010 | NAND Gate | Motorola |
| MC3003 | OR Gate | Motorola |
| LED | Light emitting diode | Hewlett-Packard |

THE OPERATION OF THE APPARATUS

A patient having tissue 14 is placed recumbent on an examination table and the electrocardiograph 16 is attached. The orthogonal microphone sensor array 22 of the sonic locater is suspended by means of an appropriate stand over the patient's chest. The ultrasonic transducer probe 12 with spark gap transmitter means 18 attached to it is placed on the chest over the heart and acoustically coupled to the skin by a suitable jelly or oil. The real-time ultrasonic scanner 2 is continuously operating and presenting a real-time dynamic two-dimensional cross-sectional image of the heart underlying the probe. The acoustical (ultrasonic) waves generated by the transducer probe are transmitted into the tissues in short pulses. Reflections of the waves occur when they traverse an interface between tissues having different acoustical properties. When the incident waves are nearly perpendicular to the interface the echoes will return to the transmitting transducer. Since the velocity of the waves is practically constant measurement of the elasped time from transmission to return of an echo indicates the range of the echo-producing interface. The multiple ultrasonic beams from the probe are scanned in rapid sequence through a plane. The echoes recorded from each beam are displayed in the same sequence and combine to produce a two-dimensional image. The images are generated at the rate of 60 per second.

The operator, using the conventional scanner display, optimizes probe position and begins data collection. The probe is held steady through most of each heart beat. Near the end of each cardiac cycle its position is changed slightly to a new position for collection of additional spatially distinct data. Through a sequence of heart beats lasting five to ten minutes the probe is moved over the heart so that all of its structures and surfaces are recorded.

The three-dimensional sonic locater 4 continuously tracks the change of position of the transducer probe and assigns X, Y and Z position coordinates to each successive two-dimensional image. The temporally related image and spatial data are digitized and stored in computer memory. When data collection is complete, the data are combined into a three-dimensional image of the heart.

The fundamental assumption of stop-action imaging of the heart (King, 1972) is that the mechanical events of systole and diastole occur in a regular, predictable sequence after the R-wave when the patient has normal sinus rhythm and a constant heart rate. Echo data recorded during the same phase of successive cardiac cycles from different portions of the heart will depict the same mechanical events and may be combined to produce a complete image unblurred by cardiac motion.

Figure 6:
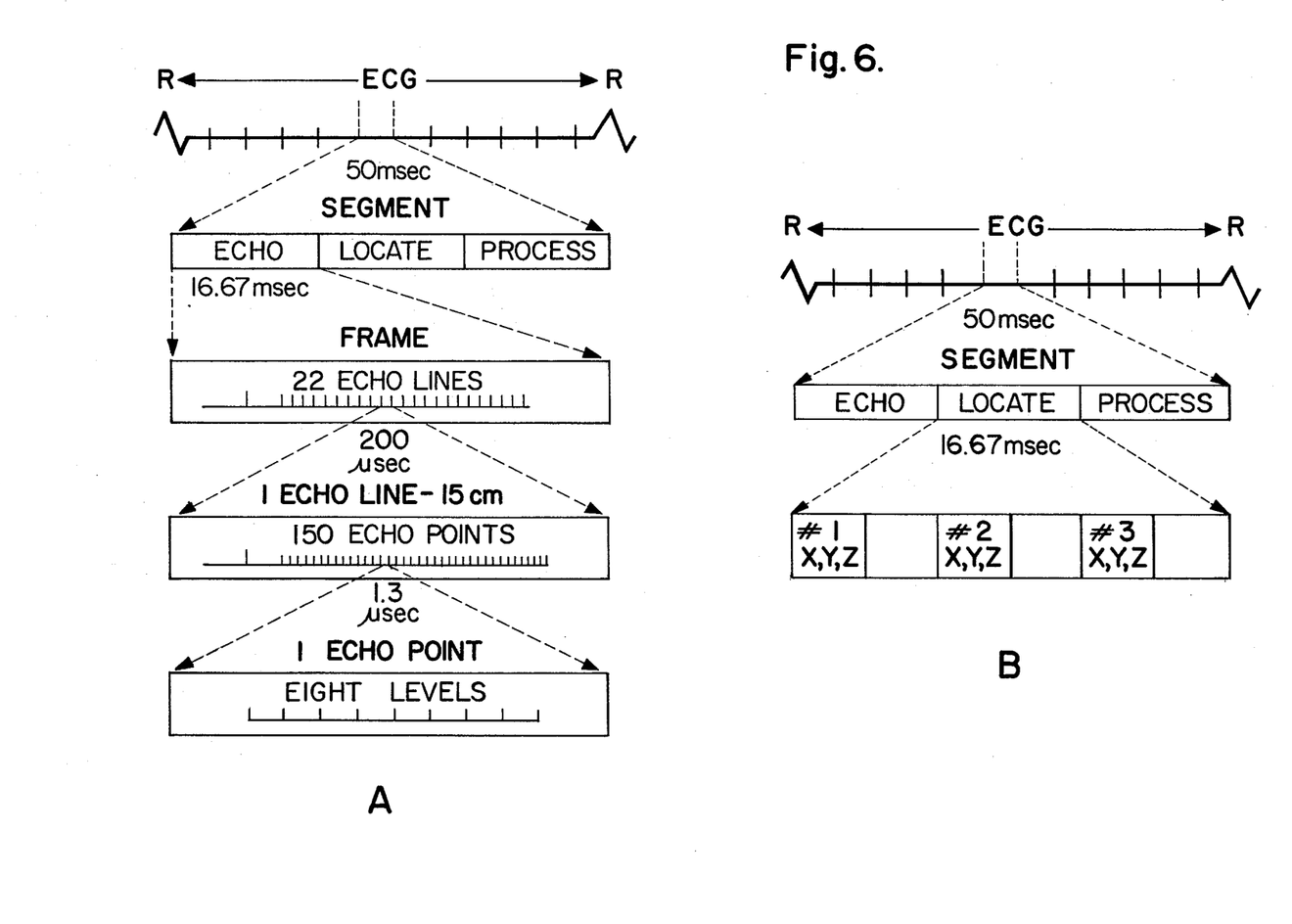
FIG. 6 is a drawing showing a graph of the R-wave segments which is referred to in the description of the operation of the system.

After initializing the system the first R-wave signal received begins its operation. Time after the R-wave is divided into segments of 50 milliseconds each, until occurrence of the next R-wave, as shown in FIG. 6. This is achieved by means of the 50-bit shift register 66. Using output signals of the shift register 66 the 50 millisecond segment is divided functionally into thirds. The first third is used for ultrasonic data collection, the second third for recording position coordinates by use of the sonic locator 4, and the last third for processing the data into computer memory 6.

The real-time scanner 2 is continuously sending 60 Hertz synchronizing and 1920 Hertz clock signals to the scheduler/controller 10 and ultrasonic data signals to the analog-to-digital converter 8. The 60 Hz synchronizing and 1920 Hz clock signals are used to identify 22 spatially and temporally distinct sound beam echo "lines" of data. These constitute a complete frame or cycle of echo data which occurs at the rate of 60 per second, or once per 16.67 msec, the duration of each third of the 50 msec segment. Immediately with occurrence of the R-wave an "enable" signal is produced which permits a "digitize" signal to go to the analog-to-digital converter 8. The digitize signal signifies the arrival at the analog-to-digital converter 8 of the first data of another echo "line". The digitize signal is repeated for each of the 22 echo "lines" of data. The data is sampled repetitively for 1.3 microsecond intervals equivalent to 1 millimeter of tissue until a total of 150 samples have been taken. The maximum value for each is digitized to one of eight levels and transferred to computer memory. One hundred and fifty samples corresponding to 15 cm. of tissue are digitized for each sound beam. All 22 echo "lines" or sound beams of a single frame or cycle of the real-time scanner are digitized prior to disabling of the digitize signal by the shift register 66.

The second third of the 50 msec segment defined by the shift register is used by the three-dimensional sonic locater. During this time each spark gap is fired in sequence as shown in FIG. 2. The transit time of the sound waves from each of the three spark gaps to each microphone 22 is measured. Subsequently the X, Y and Z coordinates of each spark gap are calculated, digitized and transmitted to the computer 6. This process is completed by the end of the second third of the 50 msec segment. The last third is used for computer processing of the data. The sequence controlled by the shift register 66 is then repeated until the next R-wave. The number of segments per R—R interval depends upon the heart rate. With each subsequent R-wave a new sequence of segments is generated. With each R-wave the position of the ultrasonic probe is adjusted so that the segments for that R—R interval contain new automatic data. All segments the same duration after the R-wave will contain anatomic data at the same phase of the cardiac cycle from different parts of the heart so that they may be combined eliminating the effects of cardiac motion to produce a complete image of the heart. Data depicting the entire heart in three dimensions are collected over a long sequence of heart cycles. At the completion of examination the computer contains a file of data blocks. In each data block are identifying data and sequencing numbers as well as numbers representing each point of the 22 ultrasound echo "lines" and the nine position coordinates defining the spatial orientation of that frame of 22 echo lines. The data of the data block file are then transformed into a body image matrix — a three-dimensional image of the heart for a given segment of the R—R interval. A separate, different image is generated for each segment. The images are digital images in computer memory which may be viewed using computer graphic techniques. These images will allow accurate quantitative analysis of ventricular volume and wall motion.

I claim:

1. An apparatus for collecting three-dimensional data on the size, shape, location and nature of animal soft tissue organ structures within the animal and reconstructing the data outside the animal to provide a representation of the size, shape, location and nature of the structure in three dimensions which comprises:
    (a) a first means having:
        (i) a source transmitting acoustical waves into the tissue; and
        (ii) a receiver for receiving waves from the tissue and detecting measurable physical characteristics of the waves
    and the first means producing electronic output signals corresponding to the characteristics of the waves;
    (b) a second means having:
        (i) a transmitter means which remains in a known spatial relationship with respect to the source and receiver of the first means, and emits into space a plurality of energy waves from a plurality of discrete points; and
        (ii) a sensing means which is spaced from the transmitter means and senses each energy wave from each discrete point of the transmitter means in three dimensions known as X, Y and Z
    and the second means producing electronic output signals corresponding to each wave from the plurality of discrete points; and
    (c) a computer means electrically coupled to the first and second means receiving the output signals from the first and second means and processing and assembling the data transmitted by the signals and displaying the data in a form for determining one or more of the size, shape, location and nature of the tissue in three dimensions.

2. The apparatus as recited in claim 1 wherein the transmitter means of the second means emits three separate energy waves from three spatially separated sources.

3. The apparatus as recited in claim 1 wherein the transmitter means of the second means emits three separate energy waves from three spatially separated sources, each of these waves is received by three separate sensors in the sensing means.

4. The apparatus as recited in claim 1 wherein the second means measures the transit time of each energy wave transmitted from the transmitter means and sensed by the sensing means in the three dimensions, the second means produces output signals corresponding to the location in three dimensions of each of the plurality of discrete points.

5. The apparatus as recited in claim 1 wherein the sensing means of the second means remains stationary.

6. The apparatus as recited in claim 1 wherein the transmitter means and the sensing means in the second means are spaced apart without electrical coupling whereby the energy waves from the transmitter means pass through space to the sensing means.

7. The apparatus as recited in claim 1 wherein the transmitter means includes an electrical spark gap means which generates an acoustical energy wave.

8. The apparatus as recited in claim 1 wherein the sensing means of the second means includes an acoustical sensing means.

9. The apparatus as recited in claim 1 wherein the second means is a three dimensional non-contacting sonic locater.

10. The apparatus as recited in claim 1 wherein the first means is an ultrasonic scanner device.

11. The apparatus as recited in claim 1 wherein the first means is an ultrasonic real-time scanner device.

12. The apparatus as recited in claim 1 including an electrocardiograph means which produces data on heart tissue which is transmitted to the computer and is used to sequence and integrate data collected over a sequence of heart cycles according to phase of the cardiac cycle.

13. The apparatus as recited in claim 12 wherein the computer means includes a scheduling and controlling means electrically coupled to the first, the second means and the computer means which performs the following functions.
   (a) it receives a signal from the electrocardiograph which signifies a new heart cycle and allocates time following that signal into given segments;
   (b) it permits data collection in the computer from the first means for a portion of each given segment of time; and
   (c) it permits data collection in the computer from the second means for a portion of each given segment.

14. The apparatus as recited in claim 1 wherein the computer includes an analog-to-digital converter for entering electronic signals into the computer.

15. The apparatus as recited in claim 1 wherein the transmitter means of the second means is rigidly coupled to the first means.

16. The apparatus as recited in claim 13 wherein the computer includes an analog-to-digital converter for entering electronic signals into the computer.

* * * * *

UNITED STATES PATENT AND TRADEMARK OFFICE
CERTIFICATE OF CORRECTION

PATENT NO. : 4,100,916
DATED : July 18, 1978
INVENTOR(S) : Donald L. King

It is certified that error appears in the above—identified patent and that said Letters Patent are hereby corrected as shown below:

Under the Heading "OTHER PUBLICATIONS" line 4, "Jorunal" should read -- Journal --.

Column 1, line 34, "pulse" should read --plus--.

Column 4, line 31, "tansparencies" should read --transparencies--.

Column 6, line 38, "for" should read --from--.

Column 6, line 46, "locator" should read --locater--.

Column 9, line 23, "microsecod" should read --microsecond--.

Column 10, line 59, "locator" should read --locater--.

Column 11, line 36, "automatic" should read --anatomic--.

Column 12, Claim 1, line 21, after "means" should read --and--.

Column 12, Claim 9, line 57, "three dimensional" should be hyphenated to read --three-dimensional--.

UNITED STATES PATENT AND TRADEMARK OFFICE
CERTIFICATE OF CORRECTION

PATENT NO. : 4,100,916
DATED : July 18, 1978
INVENTOR(S) : Donald L. King

It is certified that error appears in the above-identified patent and that said Letters Patent are hereby corrected as shown below:

Column 13, Claim 13, line 5, after "Functions" delete the period (.) and insert a colon (:).

Signed and Sealed this

Sixth Day of February 1979

[SEAL]

Attest:

RUTH C. MASON
Attesting Officer

DONALD W. BANNER
Commissioner of Patents and Trademarks